United States Patent [19]

Weinblatt

[11] Patent Number: 4,659,197

[45] Date of Patent: Apr. 21, 1987

[54] EYEGLASS-FRAME-MOUNTED EYE-MOVEMENT-MONITORING APPARATUS

[76] Inventor: Lee S. Weinblatt, 797 Winthrop Rd., Teaneck, N.J. 07666

[21] Appl. No.: 652,511

[22] Filed: Sep. 20, 1984

[51] Int. Cl.⁴ .............................................. A61B 3/14
[52] U.S. Cl. .................................... 351/210; 351/158; 351/209
[58] Field of Search ....................... 351/209, 210, 158

[56] References Cited

U.S. PATENT DOCUMENTS 3,542,457 11/1970 Balding et al. ...................... 351/209
4,102,564 7/1978 Michael .
4,145,122 3/1979 Rinard et al. ....................... 351/210

OTHER PUBLICATIONS

"Methods and Designs, Survey of Eye Movement Recording Methods" by Lawrence R. Young and David Sheena (Behavior Research Methods and Instrumentation) 1975, vol. 7(5), pp. 397–429.

Primary Examiner—Rodney B. Bovernick
Assistant Examiner—P. M. Dzierzynski
Attorney, Agent, or Firm—Thomas Langer

[57] ABSTRACT

A technique is disclosed for monitoring the eye movements of a subject with apparatus that is removably attachable to the subject's own eyeglass frame. The apparatus includes a light source to bounce light off the subject's eye and a detector to sense the reflected light. Both are adjustably mounted on a support. The support includes several interlinked parts which are readily adjustable to fit the subject's eyeglass frame.

26 Claims, 5 Drawing Figures

EYEGLASS-FRAME-MOUNTED EYE-MOVEMENT-MONITORING APPARATUS

BACKGROUND OF THE INVENTION

The present invention relates to a technique for monitoring the eye movements of a subject wearing eyeglasses, and in particular to a light, unobtrusive device easily and removably mountable on any conventional eyeglass frame.

Equipment that can monitor the eye movements of a person in response to certain visual stimuli is well known. Typically, the subject would be exposed to a visual stimulus and his ocular reactions recorded by a monitoring apparatus. Such an apparatus can include a light source, visible or infrared, which is bounced off the eye into a suitable detector. The detected signal is then electronically processed to obtain a reading of the eye position at any given time. Various such technologies are discussed in the article "Methods and Designs, Survey of Eye Movement Recording Methods" by Lawrence R. Young and David Sheena in the publication Behavior Research Methods and Instrumentation 1975, Vol 7(5) pgs. 397–429.

Many applications exist for such an apparatus; these include medical diagnosis, military uses such as weapons aiming, training equipment such as aircraft simulators, sports analysis for improving visual techniques and concentration, advertisement testing, design planning as for an automobile dashboard, and testing for visual impact as of highway and store signs. In some of the listed applications, medical diagnosis and aircraft simulators for example, the eye-movement-monitoring apparatus is stationary, as is the equipment for presenting the visual stimuli, such as a video monitor. Since the latter two are fixed, the viewer is also stationary. Typically, the subject is seated and his head fixed in place by a chin rest or a bit plate. However, in some applications, the exposure to the requisite stimuli requires movement. Thus, if analysis of a baseball batter's vision as he watches a pitched ball is desired, it would be preferable to actually do that in a batter's box in a realistic situation. Likewise, in advertising applications a subject may be requested to walk down a supermarket aisle so that his response to the most eye-catching containers can be recorded. Stationary equipment obviously cannot accomplish such tasks.

Head-mounted eye-movement-monitoring equipment has been devised which obviates the need to keep the person's head fixed. Since the equipment is affixed to the subject's head, it moves with his head and provides an accurate signal regardless of how he moves it. Such devices have been used in, for example, military applications where head movement is essential (e.g. the helmet of a pilot) and even in applications where head movement is not essential but preferable. As regards the latter, a fixed position for the head is to be avoided when the monitoring session is relatively lengthy because the subject is likely to experience considerable discomfort after awhile and a commensurate decrease in concentration. Various head-mounted arrangements are available. For example, U.S. Pat. No. 4,102,564 issued July 25, 1978 to Henry L. Michael discloses a type of arrangement including light sources and sensors mounted on a helmet. U.S. Pat. No. 3,473,868 issued Oct. 21, 1969 to Young et al. discloses a spectacle frame used in eye glasses. On the frame are mounted a light source and detectors to sense the light reflected by the eye to provide horizontal and vertical eye movement measurements. However, no provision is made for specific lens prescriptions in order to make it usable by many subjects. Also, the frame is specially modified by supports secured permanently to it to carry the monitoring devices.

My U.S. patent application Ser. No. 486,031 filed Apr. 18, 1983 discloses apparatus which is advantageously usable for eyeglass wearers. An eyeglass frame is modified to include clips for removably retaining corrective lenses. As described in that application, the corrective prescription of the subject is determined and appropriate lenses are selected from a stock kept on hand at the testing site. The eyeglass frame is further modified by an arrangement for adjustably carrying the light source and eye movement detector on the frame. These are permanently affixed to the frame.

Although the arrangement described in the above-mentioned patent application is a substantial improvement over previously known devices in that it provides a light, highly portable means which is readily modifiable to the subjects's prescription, it nevertheless has several disadvantages. For example, a stock of corrective lenses must be kept on hand. Also, since only a reasonable number of such lenses can be kept readily available, the subjects's precise correction may not be available in which case only the closest available prescription will be selected. However, this may cause the subject some degree of distraction. Furthermore, since the light source, eye movement detector and scene monitor are affixed to a frame used for all subjects, a particular subject cannot use his own frame. The standard frame he must use may cause the subject some discomfort and may, thus, be the source of additional distraction.

For specific applications, regardless of whether stationary or head-mounted equipment is used, it is desirable to superimpose the subject's eye movements on the viewed scene. This, of course, requires not only eye movement monitoring equipment but also apparatus for simultaneously detecting the scene being viewed. Signals from the eye-movement-monitoring equipment and the scene detection devices are electronically combined to attain the desired superimposition. Thus, in the above-described sports situation, the batter's eye movements would be superimposed on a scene showing approach of the pitched ball toward him. Analysis is thus possible of whether he is looking properly at the ball. In advertising, a subject is shown a filmed advertisement. Both his response and the ad are monitored. Combining the two enables the determination of the portions of the advertisement to which the subject's eyes are drawn and, thus, an analysis is possible of the effectiveness of the advertisement in attracting the subject's attention, causing him to look at the desirable portions, and creating a lasting impression. See for example my U.S. Pat. No. 4,075,657 issued Feb. 21, 1978.

Equipment exists for accomplishing both aims of portability and recordal of the viewed scene. See, for example, U.S. Pat. No. 3,542,457 issued Nov. 24, 1970 to Balding et al. It discloses two helmet-mounted television cameras. One camera records an eye spot generated by an optical system for monitoring eye movement. The other camera is aimed at the scene being viewed. Signals from the two cameras are mixed to obtain the requisite superimposition. However, this and systems like it suffer from several disadvantages. The bulk and weight of the equipment can cause discomfort and fatigue. Also, the equipment blocks the vision of one and eye and reduces peripheral vision in the other. This interferes with depth perception and is a constant reminder of the test situation and can, therefore, result in distorted responses. Eyeglass wearers cannot use the equipment because the lenses can distort the light from the optical monitoring equipment and since the apparatus leaves too little clearance to accommodate glasses. In addition, such equipment cannot readily be calibrated for the eye shape of individual subjects.

The invention applies the corneal reflection method to monitor eye movement. (See the above-mentioned Young and Sheena article). Eye movement monitoring techniques using the corneal reflection method must deal with another source of inaccuracy caused by the irregular shape of the eye. In calibrating the testing apparatus used in implementing such a technique, the subject is asked to look in the center of the displayed scene which may be on a video monitor for example, and the signal picked up from his eye with this monitoring equipment is adjusted so that the resulting dot appears in the center of the video monitor. Thus, the place where the subject is looking and the dot generated by the monitoring equipment are made to coincide. The subject is then asked to look at the upper right hand corner of the displayed image, and the apparatus is calibrated, as by operating a zoom lens, to place the signal detected from the eye at the upper right hand corner of the video monitor. In this manner, the monitored range of eye movement is adjusted so it is equivalent to the size of the scene being viewed by the subject. Were the subject's eye perfectly spherical, eye motion to the lower left hand corner of the displayed scene would accordingly place the resulting signal at the corresponding corner of the monitor. However, due to the imperfect shape of the eye, this usually does not occur. Thus, a correction must be provided so that eye motion to any part of the screen is correctly and accurately detected, recorded and interpreted despite the distinct eye imperfections of individual subjects.

SUMMARY OF THE INVENTION

It is a general object of the invention to provide an improved eye movement monitoring apparatus.

It is another object of the invention to provide an eye movement monitoring apparatus which can be worn on an eyeglass frame.

A further object of the invention is to provide an eye movement monitoring apparatus which can be removably secured to the eyeglass frame of any individual.

Yet another object of the invention is to provide a light, compact, relatively inexpensive and unobtrusive eye movement monitoring apparatus that is removably securable to the eyeglass frame of any individual.

Still another object of the invention is to provide an eye movement monitoring apparatus that is removably securable to the eyeglass frame of any individual in such a manner that it can be conveniently and quickly secured to and removed from the eyeglass frame.

Another object of the invention is to combine the monitored eye movement signals with signals indicative of the scene being viewed by the subject while his eye movements are being monitored.

One other object of the invention is to provide a correction for imperfection in the eye shape of individuals which tend to distort the monitored eye movements.

These and other objects of the invention are accomplished by one aspect of the invention directed to apparatus adapted to be mounted on an eyeglass frame for monitoring eye movements of a subject wearing this frame. The apparatus comprises support, fastening means for removably securing the support to this frame, and detector means carried by the support for sensing the eye movements of the subject.

Another aspect of the invention is directed to an eye-movement-monitoring system for monitoring the eye movements of a subject who is viewing a scene which comprises eye-movement-detection means removably mounted on the eyeglass frame normally worn by the subject, means for superimposing the output from the eye-movement-detection means over the scene being viewed by the subject, and transfer means for coupling the eye-movement-detection means to the superimposing means.

These and other aspects of the invention will be explained below in the detailed description of the drawings which is to be read and interpreted in connection with the following drawings.

DETAILED DESCRIPTION OF THE DRAWINGS

Figure 1:
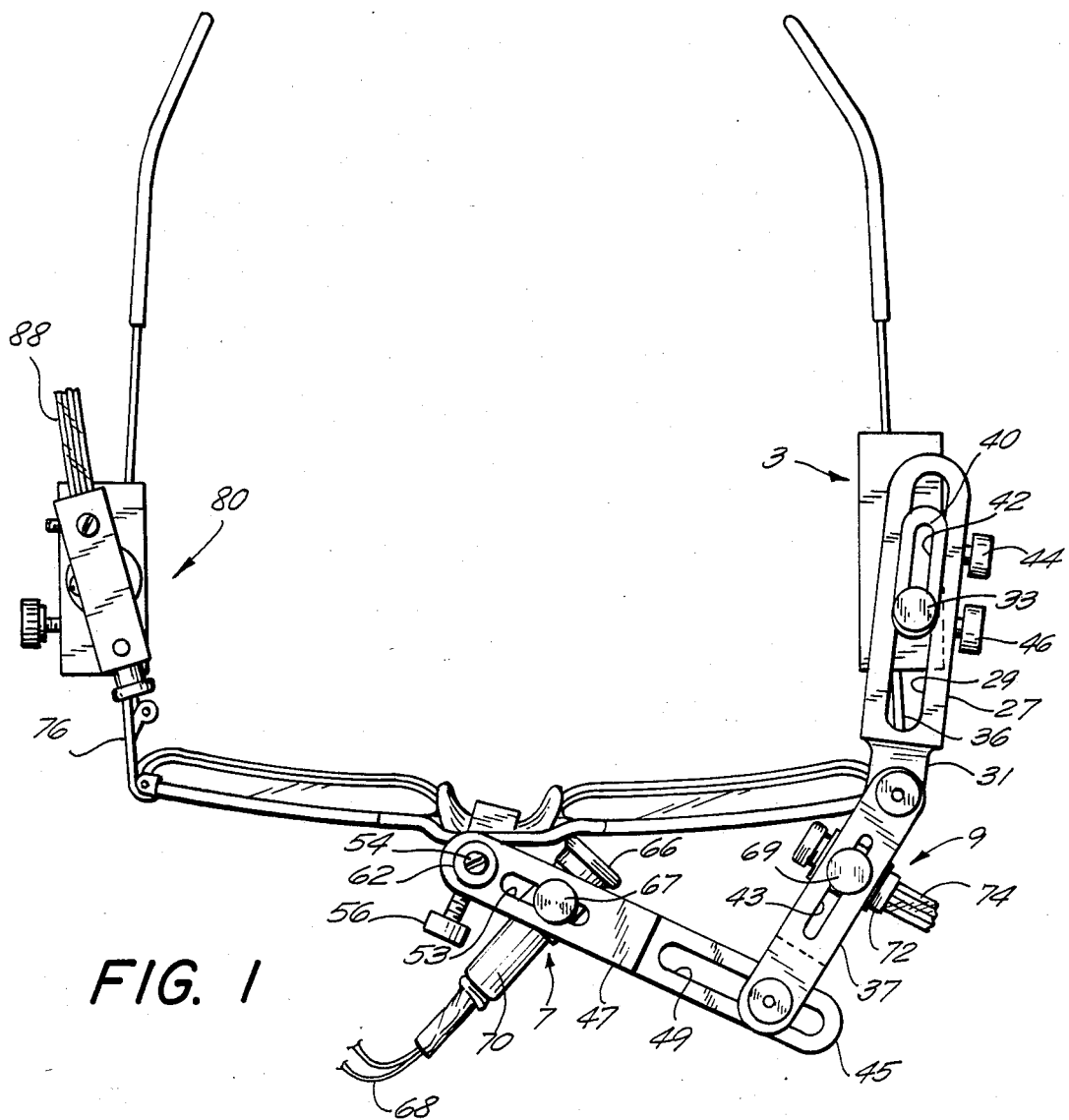
FIG. 1 is a top view of the preferred embodiment of the invention.

The preferred embodiment of the invention is comprised of the following parts: a support 3 for removably mounting the eyeglass mounted assembly 1 to an eyeglass frame, adjustment means 5 coupled to support 3 for customizing the assembly 1 to the size and configuration of the subject's particular frame, light source means 7 and detection means 9 mounted on the adjustment means in a manner enabling further adjustment of each, respectively, and optical means 11 for combining the scene and eye movement images in order to superimpose the subject's eye movement on the scene being viewed. Each of these parts is described in detail below.

Figure 4:
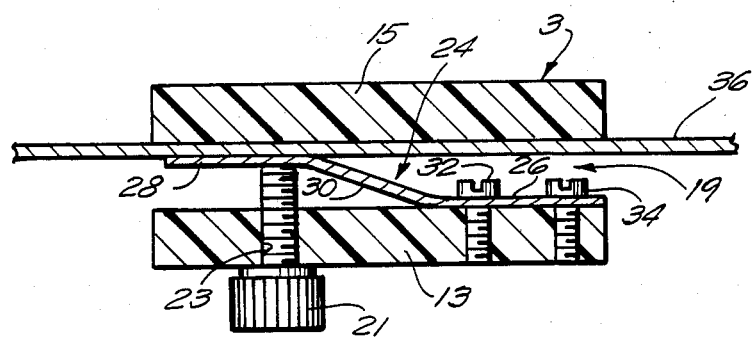
FIG. 4 is a cross-sectional view taken along line 4—4 of FIG. 3.
Figure 2:
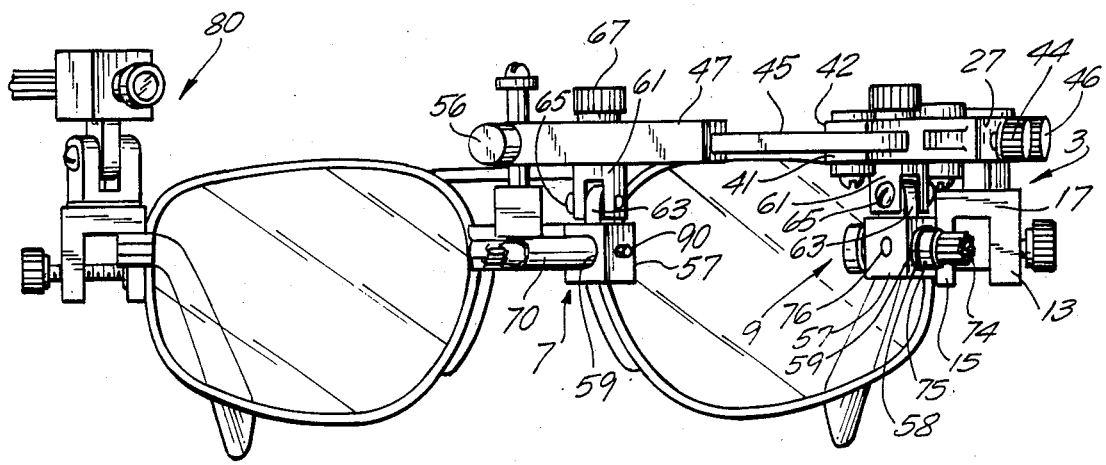
FIG. 2 is a front view of the embodiment in FIG. 1.

As best shown in FIGS. 2 and 4, support 3 includes a generally U-shaped bar with side walls 13 and 15 joined by top wall 17 to form channel 19. Walls 13 and 17 are somewhat thicker than wall 15 because the former each must be tapped to accommodate a screw (as described in detail below). The added thickness allows for tapping an effective number of turns for the screw to be adequately held in place. Although side wall 15 is relatively thin, it is rigid and strong enough to withstand the pressure applied to it by turning of the screw in wall 13.

Screw 21 is threaded into hole 23 tapped into wall 13 respectively (See FIG. 4). Screw 21 is long enough to extend through side wall 13 and into channel 19 (see FIG. 3). Strip 24 is made of a durable and resilient metal or metal alloy. It is bent to have its end sections 26 and 28 joined by an angled center portion 30. When end section 26 is secured to wall 13 of support 3, as with screws 32 and 34, the other end section 28 remains spaced from wall 15 by a distance sufficient to receive the temple piece of an eyeglass frame. As support 3 is placed over the temple piece 36 of eyeglass frame 38, top wall 17 rests on temple piece 36 while side walls 13 and 15 are slightly spaced from it. Strip 24 may also be spaced from it or just touching it. Screw 21 is tightened until the temple piece is secured between strip 24 and side wall 15. Thus, the length of screw 21 is such as to accommodate the thinnest glass frames while channel 19 must be wide enough to accommodate the thickest glass frames.

Adjustment means 5 is comprised of three bars linked together with one being linked to support 3. More specifically, bar 27 is generally rectangular and has a slot 29 and a tongue 31 as its characteristic features. Slot 29 runs along much of the length of bar 27 and snugly accommodates a slide 40 which, in turn has a slot 42 to receive the shaft of screw 33. Screw 33 is inserted into a tapped hole (not shown) at one end of support 3 and has a head bigger than the width of slot 42. When screw 33 is turned into support 3, its head bears against slide 40 to secure it in place. Screws 44 and 46 are usable to tighten bar 27 to slide 40. These screws are received within tapped holes 28 (not shown) in bar 27 and, when turned, the screw tips bear firmly against slide 40 to secure the two pieces to each other. Slide 40 adds additional freedom of movement to adjustment means 5 in two ways. Firstly, slot 42 contributes to the available distance bar 27 can be moved relative to support 3. The distance is equal to the length of both slots 29 and 42, rather than what otherwise would only be the length of slot 29. Thus support 3 may be put a little further back on temple piece 36 should that be convenient. Secondly, since temple pieces and nose bridges have relative heights which vary quite a bit on eyeglass frames of different types, slide 40 enables bar 27 to be adjusted vertically relative to support 3 so the fit on the nose bridge is precise (see below for more details). Screws 44 and 46 perform this tightening function also, of course. It should be noted that only one of screws 44 and 46 is required to bear against bar 27, not both. Which one is used depends on the relative positions of bar 27 and slide 40. It should also be noted that a plurality of tapped holes 28 (see FIG. 3) is provided along the length of bar 27. Depending on what position is selected between bar 27 and slide 40, one or both of screws 44 and 46 is placed into the appropriate hole 28. The alternative of having a screw in each of these holes is to be avoided in order to minimize weight. This arrangement provides adjustability in both rotational and longitudinal and directions. Thus, support 3 can be placed in the most appropriate location on temple piece 36 of the subject's frame and bar 27 is then moved backward, forward, or rotationally to bring the rest of the assembly into proper position, as described in more detail below.

Figure 3:
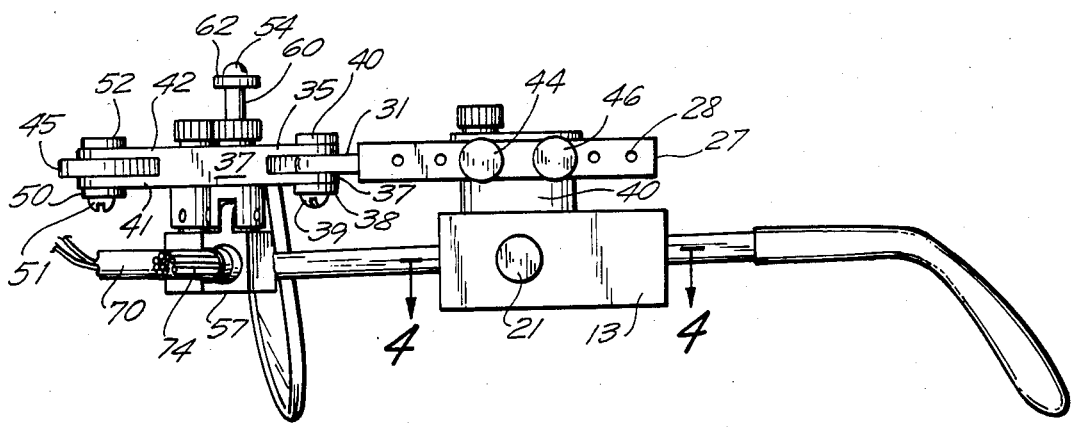
FIG. 3 is a side view of the FIG. 1 embodiment.

Tongue 31 fits between prongs 35 of bar 37, as best seen in FIG. 3. Holes, not shown, in tongue 31 and prongs 35 receive a screw 39 which also passes through washers 38 and 40. Washer 38 is tapped to act like a nut. Bars 27 and 37, thus, rotatably coupled to each other. They are tightened into position relative to each other with screw 39. It is unnecessary to fully tignten screw 39. Since assembly 1 is really secured in place to the eyeglass frame at its ends (see below), screw 39 along with washers 38 and 40 are used to establish sufficient friction between the prongs on the tongue to keep the assembly from being loose and rotating too easily and therefore uncontrollably.

The other end of bar 37 has another set of prongs, 41 and 42. It also includes a slot 43 the reason for which will be discussed below. Prongs 41 and 42 receive tongue 45 of bar 47 therebetween, as best seen in FIG. 3. Tongue 45 includes a slot 49. Screw 51 is inserted through holes (not shown) in prongs 41, 42 and slot 49, and it also passes through washers 50 and 52. Washer 52 is tapped to act as a nut for screw 51. This arrangement permits bars 37 and 47 to slide and rotate relative to each other. They are fixed in position relative to each other when screw 51 is sufficiently tightened. Bar 47 further includes a slot 53 and a hole (not shown) at the end remote from tongue 45. Received in such a hole is screw 54 within a sleeve 60 having a flared head 62 and an elongated smooth shaft. Screw 54 is threaded into a tapped hole (not shown) in grip element 55. Grip element 55 has a U-shaped cross section so it can straddle the nose bridge. Screw 56 is inserted into a tapped hole (not shown) in bar 47 and can be tightened to bear against the sleeve 60. Screw 56 and the elongated shaft of sleeve 60 enable vertical adjustment of nose-bridge grip element 55 relative to the rest of adjustment means 5. This, as said above with regard to slide 40, allows adaptation of this arrangement to eyeglass frames which vary as to relative position of the nose bridge and temple piece.

Light source means 7 and detection means 9 are best shown in FIGS. 1 and 2. The two have supports which are identical in that they provide adjustable retainers having a box 57 with an opening 59 therein and a carrier 61. Carrier 61 is U-shaped and has a tapped hole (not shown) in the top and openings in the side walls. Upward extending tongue 63 of box 57 also has a hole (not shown) and fits between the side walls of carrier 61. Screw 65 is used to rotationally couple and secure carrier 61 to box 57. Screw 67 provides rotational and longitudinal adjustment of light source means 7 to bar 47 within slot 53 while screw 69 does likewise within slot 43 of bar 37. Both screws 67 and 69 have knurled, grippable head to facilitate making the necessary adjustments as the equipment is worn by the subject.

Light source mean 7 utilizes a grain bulb and also an optical arrangement (not shown) within tip 66. Wires 68 are connected to supply power from a suitable source (not shown). The optical arrangment is conventional in that it focuses the light from the grain bulb to a point a preset distance from tip 66. Tip 66 has a smooth barrel 70 so it can slide in and out of box 57 to enable the operator to place the focused beam on the subject's eye. Set screw 90 in box 57 is then turned to secure barrel 70 in place.

Detection means 9 includes a terminator 72 to which fiber optic 74 is attached. An optical arrangement including conventional lenses (not shown) is included in terminator 7 to pick up the light reflected off the subject's eye. Set screw 76 is threaded into box 57 and is used to secure terminator 72 in place.

Although it is not a part of this invention, a scene monitoring device 80 is shown in the drawings. It is disclosed in copending application Ser. No. 572,818 filed Jan. 23, 1984. It is mounted on temple piece 76 and is aimed at the scene being viewed by the subject. It detects the viewed scene and conveys it by way of fiber optic 88 to apparatus which combines the scene with the subject's eye movements, as discussed in detail below.

Figure 5:
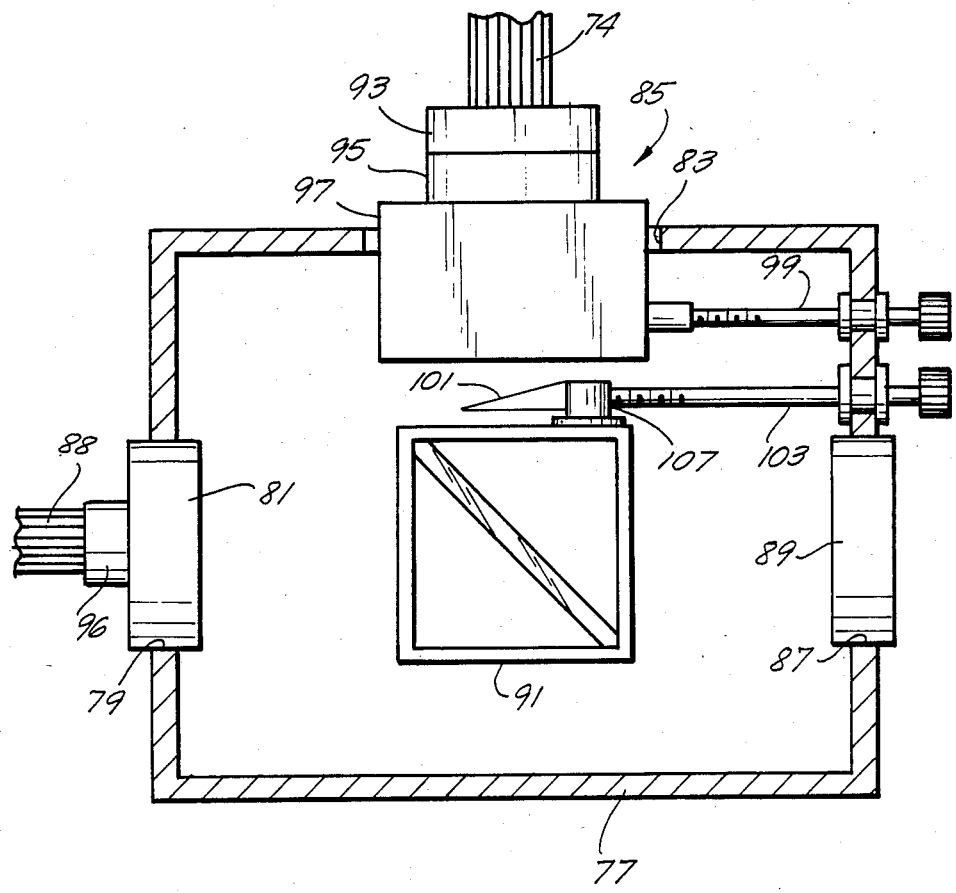
FIG. 5 is a cross-sectional view of an optical system for combining the eye movement and scene images.

Turning now to FIG. 5, an optical means 11 is shown for combining the light received from the monitored eye movement and the scene detector. Housing 77 has three openings therein. Opening 79 receives lens means 81 from the scene detectors, opening 83 accommodates lens means 85 from the eye movement monitoring means, and opening 87 receives a coupling lens 89 to video cameras (not shown). Mounted within housing 77 is a semi-silvered mirror arrangement 91. This is a well known element for both transmitting and reflecting light. Lens means 81, 85 and 89 are aligned with mirror 91 so that light from means 81 is transmitted through mirror 91 into the video camera while light from means 85 is reflected by mirror 91, also into the video camera. Thus, the video camera "sees" light from both the eye movement monitor and the scene monitor to achieve the desired superimposition.

Optical means 11 includes various adjustment and correctional capabilities. Zoom lens 96 is usable to control the size of the field of view as desired or appropriate. Depending on what is being tested, be it a large billboard or a magazine page, the size of the field of view will be adjusted accordingly. Lens means 85 from the eye movement monitoring devices mounted on the eyeglass frame includes a focusing lens 93, a zoom lens 95, and a movable support 97. Focus lens 93 is provided to add a degree of adjustability to control the light detected off the eye as it is transmitted to the video camera. This has the effect of improving resolution. Zoom lens 95 is used in calibrating the range of eye motion of each individual subject to correspond to the scene size provided by scene monitor 80 and adjusted by zoom lens 96. Support 97 is coupled to lead screw 99 to enable movement of support 97. As screw 99 is turned, it moves support 97 with respect to housing 77. This is done for reasons discussed below. Another such screw (not shown) is included to move support 97 along a perpendicular axis. Finally, prism 101 is coupled to screw lead 103. As screw 103 is turned, it moves prism 101 relative to housing 77 and support 97 for reasons discussed in detail below.

In operation, the equipment is mounted and calibrated as follows. The eyeglass frame is removed from the subject's head. Support 3 is placed on the temple piece near the hinge if possible, and screw 21 is turned to press strip 24 against the temple piece. The various elements of adjustment means 5 are then manipulated so that grip element 55 can be placed on the nose bridge of the eyeglass frame. This involves rotation and sliding of the various links as well as height adjustment using slide 40 and sleeve 60 to compensate for the height differential that exists, if any, between the nose bridge and temple piece. The object is to have light source means 7 and detection means 9 at approximately the same height. FIG. 2 shows them horizontal to each other, and this is how it should be.

The eyeglass frame is then placed on the subject's head and the light source is then activated. The equipment operator slides the barrel 70 of the light source relative to box 57 until he sees the emitted dot of light focused on the camera. This may require movement and rotation of box 57 relative to bar 47 until the dot is properly placed. Once this is done, screw 67 is tightened to secure the light source means 7 relative to bar 47 and set screw 70 is tightened to secure the barrel 70 in place relative to box 57.

Scene detector means 80 is then placed on the eyeglass frame or, of course, it could have been placed together with the eye movement monitoring apparatus. Optic fiber 88 from the scene monitor means 87 and optic fiber 74 from the eye movement monitoring apparatus are coupled to optic means 11 as described above.

The lens of scene monitor 80 is aimed at the scene and zoom lens 96 is adjusted so the desired portion of the scene substantially fills the video monitor (not shown). The subject is then asked to look at the center of the displayed scene. Detection means 9 is then adjusted by rotating and sliding box 57 until the dot generated by light reflected by the subject's cornea is approximately also in the center of the video monitor. Screw 69 is then tightened. Further adjustment of the dot due to reflected light off the eye is done by slightly moving support 97. Of course, more precise adjustment is possible with the eyeglass frame mounted apparatus without resort to optic means 11. However, such adjustment once the eyeglasses are worn may cause the subject some discomfort. Therefore, the adjustment is preferably made with optic means 11.

The mentioned adjustment is accomplished by turning screw 99. This can be called an X-axis adjustment. A similar adjustment is made with another screw (not shown) to provide a Y-axis adjustment.

Once the eye position dot is at the center of the video monitor, the subject is asked to look at the upper right corner of the scene. If the dot does not appear there, zoom lens 95 is adjusted accordingly. This should also serve to correspondingly correct for eye travel to the lower left hand corner. However, it has been found that due to irregularities in eye shape, this may not occur as explained above.

A correction is provided for such an irregularity where eye shape results in a different incremental detected eye movement depending on whether the eye moves to the right or to the left. This is behind the use of prism 101. Prism 101 bends the light passing between support 97 and mirror 91. The extent to which the light is bent depends on where on the prism it hits. Thus, the light rays are bent less near tip 105 and more near base 107. The equipment operator determines the difference between the detected eye movement in the right and left directions by viewing a monitor on which the scene and eye movement outputs are superimposed, and then turns screw 103 until the difference is eliminated or at least minimized.

It will be apparent that several modifications can readily be made to the above-described preferred embodiment of the invention. For example, one of zoom lenses 95 and 96 can be dispensed with. Also, the focus and zoom lenses can be mounted on the eyeglass frame if the added weight is not considered a problem. All such modifications are intended to be included within the scope of this invention as defined by the following claims.

I claim:

1. Apparatus adapted to be mounted on an eyeglass frame for monitoring eye movements of a subject wearing said frame, comprising:
    a support including means for adjusting the dimensions of said support to a plurality of differently configured eyeglass frames;
    fastening means for readily securing said support to said frame and readily removing said support from said frame; and
    detector means for sensing the eye movements of said subject and including a light source means for reflecting light off the eye, a light sensor for detecting the reflected light, and wire means for activating the light source and for conveying signals detected by said sensor, all of which being carried on said support.

2. The apparatus of claim 1, wherein said support comprises a carrying surface and means accomodating said frame, said accomodating means being removably securable to the frame by the fastening means.

3. The apparatus of claim 1, wherein said support comprises a generally U-shaped bar having a channel wider than said eyeglass frame, said channel being bounded by two side walls and a top wall; and said fastening means comprises at least one hole tapped into one of said side walls, and a screw threaded into said at least one wall which, when turned, secures the eyeglass frame betwen the tip of said screw and the other of said side walls.

4. The apparatus of claim 2 wherein said adjusting means comprises support bar means adjustably secured to said carrying surface of said support, said sensor being attached to the support bar means.

5. The apparatus of claim 4, wherein said support bar means enables movement of said sensor means in at least two degrees of freedom.

6. The apparatus of claim 5, wherein said support bar means comprises a first support bar adjustably secured to said support and a second support bar adjustably secured to said first support bar, said sensor means being carried by the second support bar.

7. The apparatus of claim 6, wherein said support bar means includes an extension means between the carrying surface and said first support bar.

8. The apparatus of claim 7, wherein said light source is attached to said support bar means.

9. The apparatus of claim 8, wherein said light source is carried on a third support bar adjustably secured to the second support bar.

10. The apparatus of claim 9, wherein said sensor is adjustably connected to the second support bar and the light source is adjustably connected to the third support bar.

11. The apparatus of claim 10 wherein the end of the third support bar remote from its connection to the second support bar is connected to a nose bridge grip securable to the nose bridge of the eyeglass frame.

12. The apparatus of claim 11, wherein the nose bridge grip is coupled to the third support bar and the first support bar is coupled to the support, respectively, by vertically adjustable means.

13. The apparatus of claim 12, wherein the first support bar is rotatably secured toward one end to the support and toward its other end to the second support bar, said second support bar being rotatably secured near its ends, respectively to the first and third support bars.

14. The apparatus of claim 13, wherein the first, second and third support bars are adjustably secured to each other with pins of one bar sliding, respectively, in a slot of another bar.

15. The apparatus of claim 14, further comprising means for monitoring a scene being viewed by the subject, and second support means removably secured to said eyeglass frame for carrying said scene monitoring means.

16. The apparatus of claim 15, further comprising means for superimposing the images detected by said scene monitoring means and said detector means to provide a combined image of the scene and the subject's eye movements.

17. The apparatus of claim 16, wherein said means for superimposing is optical and comprises a housing to which is secured a first lens means which is coupled to said detector means, and a second lens means for picking up light from said first lens means, whereby the second lens means transmits light to a video camera.

18. The apparatus of claim 17, wherein said detector means is coupled to the first lens means by an optic fiber.

19. The apparatus of claim 18, further comprising means to adjust the position of said first lens means relative to said housing.

20. The apparatus of claim 17, further comprising means to adjust the position of said first lens means relative to said housing.

21. The apparatus of claim 20, further comprising a prism interposed within said housing in the path of light between the first lens means and said second lens means, and means to adjust the position of said prism relative to said first lens means.

22. The apparatus of claim 17, further comprising a prism interposed within said housing in the path of light between the first lens means and said second lens means, and means to adjust the position of said prism relative to said first lens means.

23. The apparatus of claim 22, further comprising a a third lens means coupled to said scene monitoring means, said third lens means being secured to said housing and aimed so that light from it is picked up by the second lens means.

24. The apparatus of claim 21, further comprising a a third lens means coupled to said scene monitoring means, said third lens means being secured to said housing and aimed so that light from it is picked up by the second lens means.

25. The system of claim 21, further comprising a semi-silvered mirror secured in said housing with the first and third lens means being aimed to direct light therefrom at said mirror, and said second lens means being aimed to pick up the light from both first and third lens means via said mirror.

26. The system of claim 25, wherein said prism is positioned between the first lens means and said mirror.

* * * * *